US00PP19959P2

(12) United States Plant Patent
Drane et al.

(10) Patent No.: US PP19,959 P2
(45) Date of Patent: Apr. 28, 2009

(54) ***CORDYLINE* PLANT NAMED 'PINK JOY'**

(50) Latin Name: *Cordyline brasiliensis*
Varietal Denomination: Pink Joy

(76) Inventors: Walter John Drane, 825 Carmody Lane, Ningi, Queensland (AU), 4511; Doreen Joy Drane, 825 Carmody Lane, Ningi, Queensland (AU), 4511

( * ) Notice: Subject to any disclaimer, the term of this patent is extended or adjusted under 35 U.S.C. 154(b) by 0 days.

(21) Appl. No.: 12/070,187

(22) Filed: Feb. 15, 2008

(51) Int. Cl.
*A01H 5/00* (2006.01)

(52) U.S. Cl. ..... Plt./383
(58) Field of Classification Search ..... Plt./383
See application file for complete search history.

*Primary Examiner*—Annette H Para
*Assistant Examiner*—S. B. McCormick Ewoldt

(57) ABSTRACT

A new and distinct *Cordyline* cultivar named 'Pink Joy' is disclosed, characterized by very stable, strongly variegated foliage of pink/green/cream and excellent performance in drought and high heat.

1 Drawing Sheet

Figure 1:
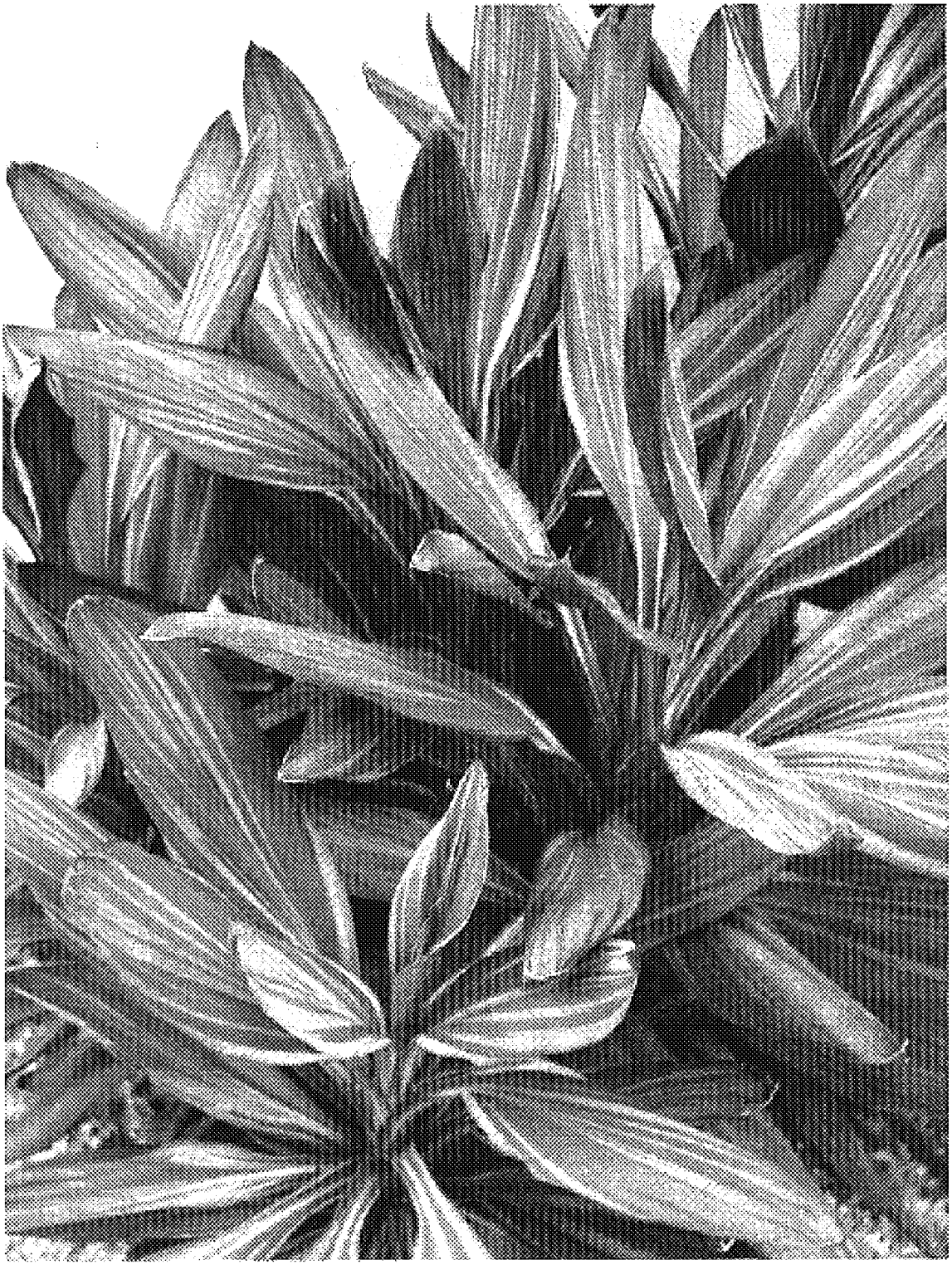

Latin name of the genus and species: *Cordyline brasiliensis*.
Variety denomination: 'PINK JOY'.

BACKGROUND OF THE INVENTION

The new variety originated as a naturally occurring mutation from the parent variety Cordyling brasiliensis 'Glauca,' an unpatented variety. The color variation was discovered at a commercial nursery in Ningi, Queensland, Australia by the inventors, Walter John Drane and Doreen Joy Drane in 1998.

Asexual reproduction of the new cultivar 'Pink Joy' was first performed in Ninji, Queensland Australia by vegetative cuttings. Multiple generations showed the distinctive pink margin to be stable and true to type, not returning to the solid green foliage of the parent variety. Subsequently 'Pink Joy' has been reproduced by micro-propagation and has shown that the unique features of this cultivar are stable and reproduced true to type through multiple generations.

SUMMARY OF THE INVENTION

The cultivar 'Pink Joy' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Pink Joy' These characteristics in combination distinguish 'Pink Joy' as a new and distinct *Cordyline* cultivar:

1. Strongly variegated foliage of green, pink and white.
2. Unique, stable pink margin.
3. Generally compact growth habit.
4. Stable and consistent foliage variegation.

Plants of the new cultivar 'Pink Joy' are similar to plants of the parent variety; *Cordyline brasiliensis* 'Glauca', in most horticultural characteristics, however, plants of the new cultivar 'Pink Joy' has a strong, colorful foliage variegation while the parent 'Glauca' has solid green foliage.

The most similar commercial *Cordyline brasiliensis* variety available to compare to 'Pink Joy' is the parent variety.

No other similar varieties of *Cordyline brasiliensis* have been identified in commercial trade.

BRIEF DESCRIPTION OF THE PHOTOGRAPH

The accompanying photograph in FIG. 1 illustrates in full color a typical plant of 'Pink Joy' grown outdoors. This plant is approximately 1 year old, shown planted in a cultivated garden area. The photograph was taken using conventional techniques and although colors may appear different from actual colors due to light reflectance it is as accurate as possible by conventional photographic techniques.

DETAILED BOTANICAL DESCRIPTION

In the following description, color references are made to the Royal Horticultural Society Colour Chart except where general terms of ordinary dictionary significance are used. The following observations and measurements describe 'Pink Joy' plants grown in a shadehouse in Ninji, Queensland, Australia from 2001 to 2003. Temperatures ranged from 5° C. t. 12° C. at night and 5° C. to 20° C. during the day. Measurements and numerical values represent averages of typical plant types.

Botanical classification: *Cordyline brasiliensis* cultivar 'Pink Joy.'

PROPAGATION

Time to Rooting: 14 to 21 days at approximately 15° C. soil temperature, 25° C. air temperature.
Root Description: Fine, fibrous.

PLANT

Height: Approximately 30 cm in a 6 inch pot. Approximately 50 cm after one year planted in the ground in a garden.
Plant Spread: Approximately 20 cm in a 6 inch pot. Approximately 40 cm after one year planted in the ground in a garden.
Growth Rate: Approximately 50 cm per annum, reaching a maximum height of approximately 1 meter at maturity.

Branching Characteristics: Left undisturbed, growth habit is upright, non-branching. However, variety will branch strongly once the terminal growing tip is removed.
Diameter of Stem: Approximately 2 cm.
Number of Leaves per Stem: Approximately 50.
Age of Plant Described: Approximately 1 year.

FOLIAGE

Leaf:

*Arrangement.*—Whorled.
*Average length.*—Approximately 15 cm.
*Average width.*—Approximately 4 cm.
*Leaf internode length.*—Approximately 1 cm.
*Shape of blade.*—Linear.
*Apex.*—Sharply acute.
*Margin.*—Entire.
*Texture of top surface.*—Smooth, glossy.
*Texture of bottom surface.*—Smooth, leathery.
*Color.*—Young foliage upper side: Background coloration is Near R.H.S. Greyed-Green 189A and Yellow-Green 147A, with overlay hue of Brown 200A. Veinal stripes are near Greyed-Green 189D. Variegated stripes of Greyed-Purple 186C and 186D. Young foliage under side: Background coloration Near R.H.S. Greyed-Green 189A with overlay hue of Brown 200A. Veinal stripes are near Greyed-Green 189D. Variegated stripes of Greyed-Purple 186C and 186D. Mature foliage upper side: The background coloration is Near R.H.S. Greyed-Green 189A and Yellow-Green 147A. Veinal stripes are near Greyed-Green 189C and 189D. Variegated stripes of Greyed-Purple 186A and Red-Purple 58B. Mature foliage under side: The background coloration is Near R.H.S. Yellow-Green 147A and Greyed-Green 189A. Veinal stripes are near Greyed-Green 189C and 189D. Variegated stripes of Greyed-Purple 186A and Red-Purple 58C.
*Venation.*—Type. Linear. Venation coloration. Near RHS Greyed-Green 189A.

Petiole: Present, however, not strongly defined from leaf-blade.

FLOWER

Has not been observed in the new cultivar, and is not commercially important. Under most commercial applications flowering will not occur.

OTHER CHARACTERISTICS

Disease Resistance: Pink Joy does not appear to be more or less susceptible to common *cordyline* diseases compared to other similar varieties.
Drought Tolerance and Cold Tolerance: Hardy to 5° C. Tolerates temperatures up to 40° C. Drought tolerance is considered good, with the variety preferring low soil moisture.
Fruit/Seed Production: Not observed.

What is claimed is:

1. A new and distinct cultivar of *Cordyline* plant named 'Pink Joy' as herein illustrated and described.

* * * * *